United States Patent [19] | [11] Patent Number: 4,940,670
Rhodes | [45] Date of Patent: Jul. 10, 1990

[54] METHOD FOR COMPOUNDING AND TESTING PATIENT SPECIFIC MONOCLONAL ANTIBODIES AND MONOCLONAL ANTIBODY FRAGMENTS FOR IN VIVO USE

[76] Inventor: Buck A. Rhodes, 1104 Stanford Dr., NE., Albuquerque, N. Mex. 87106

[21] Appl. No.: 849,741

[22] Filed: Apr. 9, 1986

Related U.S. Application Data

[63] Continuation-in-part of Ser. No. 821,999, Jan. 24, 1986.

[51] Int. Cl.$^5$ ............... A61K 39/395; G01N 33/574; G01N 33/577

[52] U.S. Cl. .................................. 436/548; 424/1.1; 424/85.8; 424/85.91; 435/7; 436/512; 436/813; 935/107

[58] Field of Search ............... 422/56, 58, 69, 102; 436/807–810, 804, 813, 548, 512; 424/1.1, 85, 85.8, 85.91; 935/107; 435/7

[56] References Cited

U.S. PATENT DOCUMENTS

| | | | |
|---|---|---|---|
| 4,017,597 | 4/1977 | Reynolds | 436/810 |
| 4,090,920 | 5/1978 | Studer | 195/127 |
| 4,225,575 | 9/1980 | Piasio et al. | 422/57 |
| 4,276,259 | 6/1981 | Eibl et al. | 436/809 |
| 4,294,817 | 10/1981 | Burgett et al. | 422/56 |
| 4,522,918 | 6/1985 | Schlom et al. | 435/68 |
| 4,540,659 | 9/1985 | Litman et al. | 436/529 |
| 4,713,352 | 12/1987 | Bander et al. | 436/811 |
| 4,861,581 | 8/1989 | Epstein et al. | 435/7 |

FOREIGN PATENT DOCUMENTS

| | | |
|---|---|---|
| 0087898 | 9/1983 | European Pat. Off. |
| 0154686 | 9/1985 | European Pat. Off. |
| 0194789 | 9/1986 | European Pat. Off. |
| 83/03677 | 10/1983 | PCT Int'l Appl. |
| WO85/03523 | 8/1985 | PCT Int'l Appl. |
| 2147698 | 5/1985 | United Kingdom |

OTHER PUBLICATIONS

Liao et al., *Biol. Abstr.*, 87, 105854, 1989.
Nairn, *Fluorescent Protein Tracing.* 4th ed., Churchill Livingstone, Edinburgh, 1976, pp. 147–150.
G. Kwapinski, *Methodology of Investigative and Clinical Immunology,* Robert E. Krieger Publishing Co., Malabar, Fla., 1982, p. 430.
D. Y. Mason et al., in G. R. Bullock et al., (EDS.), *Techniques in Immunocytochemistry,* vol. 2, Academic Press, London, 1983, pp. 175–216.
L. Olsson et al., *Journ. Immunol. Meth.* 61, 17–32, 1983.
M. R. Suresh et al., *Anal. Biochem.,* 151, 192–195, 1985.
Hellström et al., in Baldwin et al. (EDS.), *Monoclonal Antibodies for Cancer Detection and Therapy,* Academic Press, New York, 1985, pp. 17–51.
Britton et al., in Baldwin et al. (EDS.), *Ibid,* pp. 202–221.
Marx, *Science,* 216, 283–285, 1982.
Oldham et al., *Molec. Biother.,* 1, (2), 103–113, 1988.
Beumier et al., *Journ. Nuclear Med.,* 27, 824–828, 1986.
"Melanoma Targeting with a Cocktail of Monoclonal Antibodies to Distinct Determinants of the Human HMW-MAA," by S. Matzku et al., *Journal of Nuclear Medicine,* pp. 390–397, vol. 30, No. 3, (Mar. 1989).
"Monoclonal Antibody Driven Delivery of Therapeutics," by B. Rhodes, paper presented at Advances in Drug Delivery Conference, Dallas, Tex., Dec. 7, 1988.
"Determination of the Immunoreactive Fraction of Radiolabeled Monoclonal Antibodies by Linear Extrapolation to Binding at Infinite Antigen Excess," by T. Lindmo et al., *Journal of Immunological Methods.,* pp. 77–89, vol. 72, (1984).
"Iodination and Acceptance Testing of Antibodies," by Pettit et al., in *Tumor Imaging* by S. W. Burchiel and B. A. Rhodes, Masson Publishing U.S.A., Inc., N.Y., pp. 99–109 (1982).
"Radioiodination of Antibodies for Tumor Imaging," by G. B. Saha, in *Radioimmunoimaging and Radioimmunotherapy,* by S. W. Burchiel and B. A. Rhodes, Elsevier Science Publishing Co., Inc., N.Y., pp. 171–184 (1983).
"99mTc–Labeling and Acceptance Testing of Radiolabeled Antibodies and Antibody Fragments," by B. A. Rhodes et al., in *Tumor Imaging* by S. W. Burchiel and B. A. Rhodes, Masson Publishing U.S.A., Inc., N.Y., pp. 111–123 (1982).
"Radiolabeling of Antibodies with Technetium 99m" by B. A. Rhodes and S. W. Burchiel, in *Radioimmunoimaging and Radioimmunotherapy,* by S. W. Burchiel and B. A. Rhodes, Elsevier Science Publishing Co., Inc., N.Y., pp. 207–222 (1983).

*Primary Examiner*—Sam Rosen
*Assistant Examiner*—David A. Saunders
*Attorney, Agent, or Firm*—Deborah A. Peacock

[57] ABSTRACT

A kit for compounding radiolabeled monoclonal antibodies or antibody fragments for in vivo cancer diagnosis and therapy, which provides reagents for: (1) the selection of monoclonal antibodies or antibody fragments which are specific to a tumor specimen; (2) compounding the selected antibodies with a radionuclide material; and (3) quality control testing of the resulting compound. In the method of the invention, multiple aliquots of tumor biopsy material are fixed onto separate test areas of an apparatus which permits reaction with a panel of various monoclonal antibodies or antibody fragments known to react with tumor associated antigens. If one or more of the antibodies or antibody fragments bind to the tumor specimen, the reagents and antibodies or antibody fragments contained in the kit are combined with an appropriate, commercially available radionuclide. The resulting compounded radiopharmaceutical can then be administered to a patient for immunotherapy of the tumor or for cancer detection by imaging of the tumor with an imaging device to determine the extent and location of cancerous tumors. A quality control kit is used to assure that the radionuclide has been combined with the antibodies or antibody fragments to produce a formulation which will bind the radioactivity to the patient's tumor or tumor specimen.

14 Claims, No Drawings

METHOD FOR COMPOUNDING AND TESTING PATIENT SPECIFIC MONOCLONAL ANTIBODIES AND MONOCLONAL ANTIBODY FRAGMENTS FOR IN VIVO USE

CROSS-REFERENCE TO A RELATED APPLICATION

This application is a continuation-in-part application of U.S. patent application Ser. No. 821,999, entitled METHOD AND APPARATUS FOR SELECTING ANTIBODIES OR ANTIBODY FRAGMENTS, filed on Jan. 24, 1986, the teachings of which are incorporated herein by reference.

BACKGROUND OF THE INVENTION

1. Field of the Invention

This invention relates to a method and a kit for selecting and providing components or compounds to be used in formulating or compounding a drug which is to be used in a patient for cancer detection or therapy and quality control testing of the resulting compound.

2. Description of the Prior Art

The use of compositions which emit radiation at levels which can be detected after administration to a patient is well known in the art. The use of compositions which emit radiation at levels which can destroy cancerous tissues by concentrating the radioactivity in the area of tumors after the radiolabeled composition is administered to the patient is also well known in the art. However, the effective use of these compositions is limited when administered to patients with tumors that do not express the particular antigenic determinants recognized by the antibodies used in the composition. These prior art compositions rely on the selection of antibodies using the criteria of known or estimated prevalence of a particular antigen associated with a particular type of tumor. For example, colon tumors frequently express carcinoembryonic antigen (CEA), therefore an antibody composition for colon tumor is likely to contain antibodies reactive with CEA. Such an antibody, though, may not be the most effective choice for the treatment of a particular patient's tumor. Accordingly, it is highly desirable to determine whether a particular antibody binds to a given patient's tumor, in advance, in order that this antibody may be selected for inclusion in a drug or composition which is administered to the patient. It is also desirable to quality control a compound prior to administration to a patient to assure that the compound will bind to the tumor.

Prior art solid phase systems for determining reactions between antigens and antibodies have been widely used in a variety of assay systems, particularly radioimmunoassays. In such solid phase technology, the reagent or reagents used in the testing procedure are usually immobilized by being coated or bonded to a solid phase material such as a test tube or probe, which is then immersed in the sample to be tested. Additional reagents are then added to couple the solid phase material to an indicator. Commonly used indicators include the following: (1) antibodies coupled to enzymes and then further contacted with an enzyme substrate to give a color reaction; (2) antibodies coupled to a fluorescent substance which responds to certain frequencies of light or radiation exposure, and (3) antibodies coupled to radioisotopes which are detected by radiation detection devices or systems. Some solid phase systems employ lectins or other biological molecules which provide specific linkages between molecules. Examples of inventions which teach this type of assay include: U.S. Pat. No. 4,081,244, entitled "IMMUNOASSAY PROCEDURE EMPLOYING NOVEL IMMUNOCHEMICAL COMPOSITES", to Polito et al.; U.S. Pat. No. 4,092,408, entitled "METHOD FOR SOLID PHASE IMMUNOLOGICAL ASSAY OF ANTIGEN", to Litt; and U.S. Pat. No. 4,225,575, entitled "METHOD AND APPARATUS FOR PERFORMING IN VITRO CLINICAL DIAGNOSTIC TESTS USING A SOLID PHASE ASSAY SYSTEM", to Piasio et al. These prior art methods are useful for the detection and measurement of substances such as hormones or antibodies which occur in biological fluids such as sera. A common test using this prior art method is a pregnancy test in which the hormone hCG is detected in urine or blood. These prior art methods, however, are not useful in the detection of antibodies and antigens found in a tumor specimen nor do they provide means for selecting antibodies to be used in compounding a drug to be administered to an individual patient. In addition, these prior art methods are useful only in determining the presence and concentration of antigenic substances in solutions and not in determining which antibodies will react with a sample of a specific tumor. The present invention differs from the prior art in that the test material is derived from a solid tumor rather than from a liquid, and this tumor sample is fixed to the solid phase rather than reagents.

Methods for performing multiple simultaneous solid phase assays involving antigens and antibodies have been disclosed in the prior art. U.S. Pat. No. 4,378,344, entitled "METHOD AND APPARATUS FOR PERFORMING MULTIPLE, SIMULTANEOUS IN VITRO DIAGNOSTIC TESTS USING A SOLID PHASE SYSTEM," to Zahradnic et al.; teaches an assay method which utilizes a devise comprising a receptacle and an insert, each having solid phase reagents fixed to surfaces which are made to contact the fluid sample which is being analyzed. U.S. Pat. No. 4,459,360, entitled "MULTIPLE COMPONENT BINDING ASSAY SYSTEM AND METHOD OF MAKING AND USING IT," to Marinkovich, teaches an assay method which utilizes filaments in which each thread binds a different allergen. This assay system is particularity suited for the detection of IgE class antibodies in liquid samples. These prior art patents teach the use of solid phase reagents in the detection of different substances contained in common solutions. These prior art patents, however, are useful only for the testing of liquids, and specifically only for the testing of liquids which are used for in vitro diagnostic testing. The present invention, on the other hand, uses tumor tissue as the solid phase and tests it for reactivity with a series of different solutions of known compositions. This kind of testing cannot be achieved with prior art methods and devices.

Other prior art patents relating to the detection of antigens follow. U.S. Pat. No. 3,673,410 entitled "METHOD OF EXAMINATION OF CELL SAMPLES USING A RADIOACTIVELY TAGGED DYE," to Waite et al., teaches the screening of samples of tissue for the detection of disease. U.S. Patent No. 3,856,930, entitled "METHOD OF SCREENING TISSUE SPECIMENS FOR DIAGNOSTIC EXAMINATION," to Nodine et al., is an improvement over U.S. Pat. No. 3,673,410 by providing for the automatic elimination of specimens which do not need to be examined by more thorough diagnostic methods. Significant improvements over these approaches have resulted from methods which employ solid phase presentation of samples for the determination of one or more antigens or antibodies by detection of the corresponding antibody or antigen. U.S. Pat. No. 4,187,075, entitled "METHOD OF ANALYZING BIOLOGICAL, LIQUID SPECIMENS FOR ANTIGENS OR ANTIBODIES," to Noller, describes a method for detecting either an antigen or antibody in a solid phase presentation of a human body fluid. U.S. Pat. No. 4,495,295, entitled "IMMUNOASSAYS USING SUPPORT-CONTAINING SEPARATE ANTIGENS AND ANTIBODIES DERIVED FROM AN IMMUNE COMPLEX," to Neurath, improves upon previous methods for detecting antigens or antibodies by employing a dissociating buffer during the process to separate antigen-antibody complexes. U.S. Pat. No. 4,495,296, entitled "LABELED ANTI-HAPTEN ANTIBODIES AND THEIR USE AS A UNIVERSAL REAGENT FOR SOLID PHASE RADIO- AND/OR ENZYME-IMMUNOASSAYS," to Neurath et al., improves the detection of antigen and antibodies by employing anti-hapten antibodies as universal reagents. The present, invention improves on these previous inventions by using a panel of different antibodies in a parallel series which permit the detection of individual arrays of antigens to define the properties a given patient's tumor. The present invention provides a kit and method for matching antibodies to aliquots of tumor biopsy specimens, for selecting monoclonal antibodies to be used in compounding antibody-based drugs which are matched to the antigenic properties of a given tumor, and for quality control testing of the compounded drug.

U.S. Pat. No. 4,513,088, entitled "ASSAY FOR MONOCLONAL ANTIBODY AGAINST SURFACE IG OF A HUMAN B-CELL TUMOR," to Levy et al., describes a method for detecting antibodies by specifically screening hydridoma culture fluid for anti-idiotype antibodies. This method permits selection of antibodies useful in the treatment of human B-cell tumors. The present invention is an improvement over the Levy, et al., method because it permits selection of antibodies for the diagnosis and treatment of solid tumors. Furthermore, antibodies to general tumor associated antigens rather than to anti-idiotypic antibodies can be selected using the present invention.

The standard prior art method for determining if a specific monoclonal antibody will react with a tumor from an individual patient requires obtaining slices of the tumor, mounting the slices on a microscope slide, and staining the slice with the antibody in question. A separate microscope slide is required for each antibody when more than one antibody is being tested. An alternative prior art method is to take a sample of the tumor and treat it in such a way as to cause the individual cells of the tumor to disperse. The cells are reacted with antibodies labeled with fluorescent dye and passed through a cell sorter which counts the cells which have reacted with the antibody. Using this method, a separate cell sorter analysis is carried out for each antibody which is being tested. These prior art methods cannot be used for rapid, multi-antibody screening assays. Individual specimens have to be processed by specially trained individuals and tested one at a time for reactivity with a given antibody. Thus, these prior methods are costly, time consuming and difficult to standardize. The present invention provides for the simple and fast testing of a tumor specimen for reactivity with a panel of different antibodies, simultaneously, with quality control measures to ensure standardized testing.

A method for binding antigen to a solid phase for the detection of specific monoclonal antibodies has been reported by Suresh, M.R. and Milstein, C., *Analytical Biochemistry*, "A Direct Antigen—Binding Assay to Screen Hybridoma Supernatants." 151, 192–195 (1985). Using this method, the antigen is fixed to nitrocellulose paper spots which are attached a plastic insert. The insert is exposed to solutions which are to be assayed for the presence of antibody reactive with the fixed antigen. The presence of a specific antibody in a solution being tested is detected by exposing the nitrocellulose paper spot to a detecting solution comprising an anti-antibody conjugated to an enzyme which produces a color reaction when exposed to the appropriate enzyme substrate. This method is suitable for screening hybridomas to select those which secrete antibody which is specific for a particular antigen. This prior art method is used to find a particular antibody which may be present in the solution. This method, however, is not useful for determining which antigens are present and thus which antibodies or antibody fragments will react with a tumor specimen.

U.S. patent application Ser. No. 821,999, entitled METHOD AND APPARATUS FOR SELECTING ANTIBODIES OR ANTIBODY FRAGMENTS, discloses a method and apparatus selecting antibodies or antibody fragments for use in preparing drugs for cancer detection or therapy. The present invention is an improved method and kit for the selection, the compounding, and quality control testing of radiolabeled compounds and for the in vivo detection and treatment of cancer.

Use of prior art methods for the treatment or diagnosis of cancer often requires that a drug be administered to a patient first before determining whether or not that compound will have any beneficial effects. Even if a pre-treatment drug screening is performed for a patient, it is often too expensive to screen again. Prior art methods for screening cancer therapy drugs to predict the potential effectiveness of a given drug for use in an individual patient rely on growing tumor cells in tissue culture and exposing the growing cells to varying concentrations of different anticancer drugs. In vivo efficacy is predicted from the measured effect of the drug on the in vitro growth of the tumor cells in tissue culture. See "Applications of the Human Tumor Stem Cell Assay to New Drug Evaluation and Screening," by S.E. Salmon, *Prog. Clin. Biol. Res,* Vol 48, pp. 291–312, (1980). This prior art method is very laborious and can be used only in cases where the tumor cells can actually be grown in tissue cultures. The present invention avoids the necessity of tumor cell growth, and the necessity of measuring drug effects on tumor cell growth. An advantage of the present method is that when tumor cells undergo antigenic modification (the tumor changes its character) between treatments, the selection method of the invention can be used again to determine if different antibodies should be selected for the next treatment.

Accordingly, it is an object of the present invention to provide an inexpensive method and apparatus for selecting a panel of monoclonal antibodies which will specifically react with an individual patient's tumor.

It is a further object of the present invention to provide a method and apparatus for the simultaneous testing of several different monoclonal antibodies or antibody fragments.

Yet another object of the present invention is to provide a method and apparatus for the selection of antibodies in which a patient's tumor specimen is used as the solid phase reagent.

Another object of the present invention is to provide a kit and method for compounding antibodies or antibody fragments with a radionuclide for use in cancer detection or immunotherapy.

Another object of the present invention is to provide a method and apparatuses which contain quality control features for the standardization of antibody testing and for the testing of radiolabeled compounds or radiopharmaceuticals.

A further object of the present invention is to provide a method and an apparatus for optimizing the selection of antibodies, in advance, in the administration of drugs or compounds to an individual patient.

Other objects and further scope of applicability will become apparent from the detailed description to follow.

SUMMARY OF THE INVENTION

This invention relates to a method and kit for the selection, compounding, and quality control testing of antibodies or antibody fragment compounds for the detection and treatment of cancerous tumors. Use of the method and kit of the present invention enables the compounding of specific drugs for each individual patient's needs.

In accordance with the present invention, a method is provided for selecting antibodies or antibody fragments which bind specifically to an individual patient's tumor. The method comprises testing several antibodies simultaneously to select the antibody or antibodies which bind to a tumor from those which do not bind to the tumor. The method further comprises the compounding of selected antibodies of antibody fragments with a radionuclide.

In one method of the invention, at least one antibody or antibody fragment which is reactive with a patient's tumor is compounded with a radionuclide for use in in vivo cancer detection. The compound is subjected to a quality control test to assure that the formulation will bind the radioactive material to the specimen obtained from the patient's tumor. This compound is then administered to a patient and the patient is imaged with an imaging device to determine the extent and location of cancerous tumors.

In an alternative method of the invention, at least one selected antibody or antibody fragment is compounded with a radionuclide to formulate a radiopharmaceutical for immunotherapy of a patient's tumor. Prior to administration of the radiopharmaceutical to a patient, the compound is quality control tested to assure that the radionuclide has been adequately prepared and combined with the antibodies or antibody fragments.

The method and apparatuses of the invention are also useful in selecting and compounding antibodies or antibody fragments with chemicals for chemotherapy or with toxins for immunotoxin therapy.

The kit of the present invention provides for the selection, compounding, and quality control testing of antibodies or antibody fragments and their compounds. The kit comprises apparatuses for: (1) the selection of antibodies or antibody fragments which are reactive with a patient's tumor; (2) the compounding of a radionuclide with the selected antibody or antibody fragment; and (3) the quality control testing of the radiolabeled compound.

The selection apparatus comprises an insert and a matching receptacle. The insert comprises at least two projections which fit into the matching receptacle. In the preferred form of the invention, each projection comprises at least three test areas. The first test area is a negative control area. This area contains an antigenic substance such as bovine serum albumin which is unreactive with monoclonal antibodies specific for tumor associated antigens. The second area is the test area to which the specimen from the tumor is bound. The third area is a positive control area which contains an antigenic substance such as a homogenate of a tumor xenograft which is reactive with one of the specific monoclonal antibodies to be tested.

In an alternative embodiment of the invention, the positive control area of the selection apparatus comprises sub-areas to which varying quantities of the antigenic material are bound so that various degrees of detection will occur on the control sub-areas after testing the antibodies. The degree of detected material on the positive control areas can then be compared to the degree of detected material on the tumor test area to determine what quantity of antigen is present in the tumor. This will help determine the quantity of antibody to be used in the compound or drug to be administered to the patient.

Preferably, the receptacle and insert of the selection apparatus of the invention have complimentary configurations so that the apparatus will not be misused. For example, an insert for testing a lung cancer tumor should not be placed into a receptacle relating to a colon cancer test. Various configurations for the insert/receptacles can be achieved by having different spacings between the projections or by shaping the insert and receptacles so that only the correct insert will fit into its appropriate receptacle.

The preferred selection method of the invention, used in conjunction with the selection apparatus, for indicating which antigens are present in the tumor specimen, comprises the following steps:

(1) Homogenize a sample of a tumor taken at biopsy or surgery;

(2) Suspend the homogenate in a water or saline solution;

(3) Place aliquots of the suspended homogenate on test areas of the selection apparatus of the invention;

(4) Fix the homogenate to the test areas;

(5) Coat the test areas to which the tumor specimen has been fixed with excess antigenic material which is unreactive with monoclonal antibodies or antibody fragments specific for tumor associated antigens to assure that all residual antigen binding sites in the areas have been saturated;

(6) Bind the added antigenic material;

(7) Subject the test areas to a panel of monoclonal antibodies or antibody fragments;

(8) Wash the test areas to remove excess antibody or antibody fragments which have not reacted with antigen;

(9) Develop the washed test areas to detect the presence of antibodies or antibody fragments on a solid phase;

(10) Remove and wash the test areas to remove any remaining solution and to stop the developing reaction;

(11) Inspect the test areas to determine which, if any, antibodies or antibody fragments have reacted with the tumor specimen and preferably the intensity or degree of the reaction;

(12) Dry the test areas so that they may be used as a record of the test results, if applicable.

Use of the selection method and apparatus of the invention indicates whether there is an antigen-antibody reaction with the tumor specimen, and preferably the degree or intensity of the reaction. If there is a positive reaction, the antibody is useful in compounds or drugs to be administered to the patient. The degree or intensity of the reaction is useful in determining the quantity of antibody to be used in the compound or drug. If there is no antigen-antibody reaction as indicated by the test area, the antibody tested is contraindicated for the diagnosis or treatment of the patient's tumor.

The compounding apparatus of the present invention comprises means for mixing at least one selected antibody with a labeling reagent and a radionuclide to form a radiolabeled compound. Preferably, the compounding apparatus further comprises means, such as a filter column, to remove radionuclidic impurities from the radiolabeled compound.

The preferred compounding method of the present invention, used in conjunction with the compounding apparatus, for compounding selected antibodies with a labeling reagent and a radionuclide, comprises the following steps:

(1) Obtain at least one selected antibody for use in compounding a radiolabeled compound;

(2) Mix the antibody with a labeling reagent and a radionuclide; and (3) Filter the compound to remove radionuclidic impurities.

The quality control testing kit of the present invention preferably comprises at least three apparatuses. The first apparatus comprises a negative control test area. This test area contains an antigenic substance, such as bovine serum albumin, which will not react or will insubstantially react with the radiolabeled compound. The second apparatus comprises a tumor test area which binds a sample of the patient's tumor. The tumor test area should substantially react with the radiolabeled compound if the antibodies have been properly selected and prepared. The third apparatus comprises a positive control test area which binds an antigenic substance, such as a tumor homogenate xeno-graft, which should substantially react with the radiolabeled compound if the compound has been properly selected and prepared. The apparatuses may be used separately or together, as a kit, to quality control test the radiolabeled compound.

The preferred quality control testing method of the present invention, used in conjunction with the quality control kit, for determining whether a radiolabeled compound has been properly prepared, comprises the following steps:

(1) Subject a test area of each quality control test apparatus to a sample of a prepared radiolabeled compound;

(2) Measure the resulting radioactivity of each test area with a radiation detector;

(3) Wash the test areas to remove any unreacted compound; and (4) Measure the radioactivity of each washed test area with a radiation detector.

The percentage reactivity of each test area to the radiolabeled compound is calculated by dividing the measure of radioactivity in step (4) by the measure of radioactivity in step (2). If the compound has been prepared properly, the negative control test area will not have reacted or will have reacted only minimally with the compound. Likewise, the percentage reactivity of the positive control test area should indicate a substantial reaction with the radiolabeled compound. If the antibody or antibodies have been properly selected and the radiolabeled compound prepared properly, the percentage of immunoreactivity of the tumor test area should be high. Low levels of immunoreactivity suggest that the drug is not suitable for use in a patient for cancer detection or therapy.

These three methods and apparatuses for selection, compounding, and quality control testing may be used separately or together in a kit form. The preferred kit of the invention comprises:

(a) A selection apparatus, comprising; an insert with at least two projections, each projection containing a tumor test area; and a matching receptacle for receiving the insert and which contains at least two antibodies or antibody fragments which are potentially reactive with a tumor specimen;

(b) A compounding apparatus comprising; a receptacle for receiving and mixing the selected antibody or antibodies, a labeling reagent and a radionuclide to form a radionuclidic compound; and a filter column for purifying the formed radionuclidic compound; and (c) A quality control kit comprising at least three test apparatuses, a negative control test apparatus which contains an antigenic material which is unreactive with any of the panel of the antibodies contained in the selection apparatus, a tumor test apparatus which should indicate a substantial reaction with the radiolabeled compound if the antibodies have been properly selected and if the radiolabeled compound has been properly prepared, and a positive control test apparatus to test each of the panel of antibodies contained in the selection apparatus and which should indicate a reaction with the radiolabeled compound to the extent that the corresponding antibody is present in the compound.

Use of the kit and method of the invention provides a fast and inexpensive method to determine which antibodies should be used for an individual patient, to compound an appropriate drug, and to quality control test the drug. The kit is used prior to administering any drugs or compounds to the patient so that the treatment or diagnosis can be optimized.

DESCRIPTION OF THE PREFERRED EMBODIMENTS

This invention relates to a kit and a method for compounding radiolabeled antibodies or antibody fragments for in vivo cancer detection and therapy. The kit comprises apparatuses and reagents for: (1) selecting at least one monoclonal antibody or antibody fragment which is specific to a patient's tumor; (2) compounding the selected antibody with a radionuclide; and (3) quality control testing of the resulting radionuclidic compound. The use of the word "antibody" or "antibodies" in the description is non-limiting and is intended to refer to the singular or plural and to also include an antibody fragment or antibody fragments.

Solid phase reactions are carried out using the selection method and apparatus of the invention, permitting simultaneous testing of multiple aliquots of a tumor specimen with a panel of antibodies or antibody fragments that are potentially reactive with the tumor specimen.

The selection apparatus of the invention comprises an insert and a receptacle. The insert of the present invention comprises at least two teethlike extensions or projections, to which small volumes of tumor biopsy homogenates can be bound to test areas on each of the extensions. In the preferred embodiment of the invention, the insert comprises at least three test areas per projection. The test areas on each projection contain a binding material which will bind proteinaceous and other antigenic materials. One such binding material, useful in the selection apparatus, is nitrocellulose filter paper. Bound to a negative control test area of each projection is an antigenic substance, such as bovine serum albumin, which is unreactive with monoclonal antibodies specific for tumor associated antigens. The test area of each projection has no antigenic material bound to it. This area is reserved for fixing an aliquot of the specimen of the tumor obtained from a patient. Monoclonal antibodies to be tested are selected by matching them to antigenic determinants suspected of being present in a given type of tumor. Bound to a positive control area of each projection is an antigenic substance, such as a homogenate of a tumor xenograft, which is reactive with one of the specific monoclonal antibodies to be included in the test panel of monoclonal antibodies.

When the method of the invention has been completed, the tumor test area will have bound the antibody or antibody fragment being tested if there has been an antigen-antibody reaction, indicating that this specific antibody will bind to the tumor. As an alternative and preferred embodiment, the positive control area is subdivided into at least two sub-areas so that each of the subareas contains a different concentration of the antigenic substance. When the method of the invention has been completed, the sub-areas contain varying quantities of antibodies. These quantities are detected and compared to the quantity of antibody present on the tumor test area. This indicates the degree of antigenic material present in the tumor and thus aids in determining the quantity of antibodies to be used in compounding a drug for treatment or diagnosis.

Antigen-antibody reactions can be detected on the test areas by means, common to the art, including:

1. Darkening: An anti-antibody-peroxidase plus substrate is used for development, and detection is by visual inspection or other means.

2. Color formation: An anti-antibody-enzyme plus substrate is used for development, and detection is by visual inspection or other means.

3. Fluorescence: An anti-antibody-fluorescent dye is used for development, and detection is by the use of a fluorimeter or other means.

4. Radioactivity: An anti-antibody-radionuclide is used for development, and detection is by the use of a radiation detector or other means.

The insert of the selection apparatus of the invention matches with a receptacle. Preferably, the receptacle contains a plurality of compartments. One row of compartments preferably contains an antigenic substance such as bovine serum albumin which is unreactive with monoclonal antibodies specific for tumor associated antigens. Another row of compartments preferably contains a panel of different monoclonal antibodies which are tested to indicate whether they will bind to a specific patient's tumor. For example, when a colon tumor is being tested, different antibodies known or suspected to react with colon tumor antigens, such as CEA, would be placed in the row of compartments of the receptacle reserved for the panel of antibodies. Other compartments contain reagents for detecting the antigen-antibody reaction. The apparatus of the invention is especially useful in a kit form for testing several antibodies simultaneously.

In an alternative embodiment, the reagents and/or monoclonal antibodies may be provided to the receptacle of the invention in a lyophilized (freeze dried) form. Water, sera, or the patient's own serum may be used to reconstitute the reagents into a solution form.

The configuration of the receptacle of the selection apparatus is preferably complimentary with the configuration of the insert. Most preferably, a different configuration of receptacle and insert is made for each type of tumor to be tested. For example, a given insert/receptacle configuration is assigned to lung tumors and a different insert/receptacle configuration is assigned to colon tumors. Various configurations of the insert/receptacle could be achieved, for example, by spacing the extensions differently on each insert for each type of cancer testing apparatus, so that the insert can be fitted only one way into the correct receptacle, and so that an insert made for one type of cancer cannot be fitted into a receptacle which relates to another type of cancer. Another way to achieve different configurations for apparatuses would be to shape the inserts and receptacles differently; as an example, a lung cancer test apparatus could have round extensions on the insert which fit into round compartments in the receptacle, and a colon cancer test apparatus could have flat extensions on the insert which fit into slits in each compartment of the receptacle. Preferably, the use of different configurations for the inserts/receptacles assures that only the lung cancer insert can be employed with the receptacle containing antibodies reactive with lung cancer antigens; and only the colon cancer insert can be employed with the receptacle containing antibodies reactive with colon cancer. The advantage of using different configurations for different tumor types is to assure against misuse of the product. The use of the words "lung" and "colon" in the description of the selection apparatus is for illustrative purposes only. The apparatuses, kit, and methods of the invention are not limited to these types of cancerous tumors, but are useful in the diagnosis or treatment of any type of tumor.

The selection method of the invention comprises affixing a sample of a tumor homogenate to a solid phase test area, subjecting the sample to at least one antibody, and detecting if there has been an antigen-antibody reaction.

A preferred selection method of the invention for determining which if any of the panel of monoclonal antibodies reacts with a given tumor specimen comprises the following steps:

(1) Homogenize a sample of a tumor taken at biopsy or surgery, by means common to the art. Most preferably, the tumor homogenate is suspended in an aqueous or a saline solution prior to placing the sample on a test area. A preferred solution is a 0.05 Normal phosphate saline solution, containing approximately 0.9% by weight sodium chloride and a pH of approximately 7.4.

This solution approximates the salinity and pH normally found in a human body.

(2) Place aliquots of the tumor homogenate on test areas of the projections of the selection apparatus of the invention. The preferred volume of the aliquot of homogenate comprises between approximately 0.001 milliliter to 1.0 milliliter.

(3) Fix the homogenate to the test area. Fixing is preferably achieved by incubation, such as by incubating in a humid environment at about 25° C. for about 30 minutes.

(4) Coat the test area to which the tumor specimen has been fixed with excess antigenic material to assure that all residual antigen binding sites in the area have been saturated. One procedure of accomplishing this is to add a 1% solution of bovine serum albumin in a sufficient amount to cover the entire test area.

(5) Bind the added antigenic material. Binding is preferably accomplished by incubation, such as by incubating in a humid environment at about 25° C. for about 30 minutes. Preferably, residual non-bound antigenic material is removed by washing the projections of the insert.

(6) Place the insert into a matching receptacle which contains a panel of monoclonal antibodies. The insert is left in the receptacle for a sufficient period of time to permit the antibodies to react with the antigens that are bound to the insert. The incubation time is preferably between 1 minute and 24 hours, and most preferably approximately 30 minutes.

(7) Develop the washed insert with reagents. Most preferably, the insert is washed prior to developing to remove any antibodies which have not reacted with antigen. Preferably, the insert is developed by reacting it with a second antibody reactive with any or all of the panel of monoclonal antibodies being tested. A goat antimouse IgG which has been previously conjugated to an enzyme such as horseradish peroxidase is a preferred developing reagent. The insert is placed in a solution reactive with the developing reagent. When horseradish peroxidase is used as the developing reagent, the reactive solution is preferably a peroxide solution, and most preferably an aqueous 0.1% hydrogen peroxide solution. The peroxide solution may be generated by an enzyme substrate reaction, such as by the reaction of glucose oxidase with glucose. The antigen-antibody reaction is allowed to develop on the test area by incubating the insert for a period of time of between approximately 1 minute and 2 hours, and preferably for approximately 10 minutes. After developing, the insert is most preferably washed to remove any remaining solution and to stop the developing reaction.

(8) Detect the presence of antibodies on the solid phase insert, to determine which, if any, antibodies have reacted with the tumor specimen. Inspection may be by visual or other means of detection, common to the art, for determining if an antigen-antibody reaction has occurred. When a developing reagent such as goat antimouse IgG horseradish peroxidase - hydrogen peroxide system is used, the reaction is indicated by a darkening of the area on which the tumor specimen had been bound. The control areas on the insert are inspected or otherwise evaluated to assure that the assay has been performed correctly. For example, the areas to which the positive control antigen had been previously bound should indicate, by a darkened area, that an antigen-antibody reaction has taken place. The areas to which the negative control antigen had been previously bound should indicate, by an area that is not darkened, that no antigenantibody reaction has occurred. In an alternative embodiment in which varying amounts of control antigen are used, sub-areas of the positive control area of the insert will show a gradation of darkening. In such an embodiment, the degree of darkening of the test area to which the tumor specimen is bound is compared to the positive control area. By matching the degree of darkening of the tumor area to the gradations of the positive control area, the relative amount of reactive antigen in the tumor specimen can be estimated.

The insert may be dried to provide a record of the test results. If darkening is used as a means for detection, the insert can be photocopied so that the copy can serve as a record.

The selection method and apparatus of the present invention can also be used to determine the relative amounts of different subpopulations of leukocytes. In this application, white blood cells are separated and aliquots are attached to the test areas of the projections. The antibodies used in the receptacle are a panel of antibodies which react with specific subsets of human leukocytes, such as anti-T helper and anti-T suppressor. This method is useful to diagnose and monitor immune deficiencies that occur in cancer, autoimmune diseases, organ transplants, and immune deficiencies caused by diseases such as AIDS (Acquired Immune Deficiency Syndrome).

The compounding apparatus of the invention comprises means for mixing at least one selected antibody with a labeling reagent and a radionuclide to form a radiolabeled compound or drug. In kit form, the selected antibody and/or labeling reagent may be present in a lyophilized (freeze dried) form. Water, sera, a buffered saline solution, the patient's own serum, or other appropriate fluids may be used to reconstitute the antibodies and reagents into a solution form.

The means and method for mixing and compounding the selected antibody with the labeling reagent and radionuclide may be simply depositing measured amounts of the constituents into vials or receptacles. In kit form, syringes may be provided for extracting a measured amount of each constituent out of each of their respective vials and injecting the contents of each syringe into a common vial to accomplish mixing. More than one selected antibody may be used in mixing and formulating a compound.

The methods for labeling antibodies with radioiodine have been described in the literature. Examples of papers which present these labeling methods are: "Iodination and Acceptance Testing of Antibodies by Pettit et al, in *Tumor Imaging* by S.W. Burchiel and B.A. Rhodes, Masson Publishing USA, Inc., N.Y., pp. 99–109 (1982); and "Radioiodination of Antibodies for Tumor Imaging" by G.B. Saha, in *Radioimmunoimaging and Radioimmunotherapy* by S.W. Burchiel and B.A. Rhodes, Elsevier Science Publishing Co., Inc., N.Y., pp. 171–184 (1983).

Methods for labeling antibodies with Technetium-99m have been described in the literature: "99mTc-Labeling and Acceptance Testing of Radiolabeled Antibodies and Antibody Fragments" by B.A. Rhodes et al, in *Tumor Imaging* by S.W. Burchiel and B.A. Rhodes, Masson Publishing USA, Inc., N.Y., pp. 111–123 (1982); and "Radiolabeling of Antibodies with Technetium 99m" by B.A. Rhodes and S.W. Burchiel, in *Radioimmunoimaging and Radioimmunotherapy* by S.W. Burchiel and B.A. Rhodes, Elsevier Science Publishing Co., Inc., N.Y., pp. 207–222 (1983).

Any radionuclidic material may be used in the present invention. The above references relating to radioiodine and Technetium-99m are cited merely to describe standard methods of radiolabeling.

Preferably, in the method of the invention, the compound is purified by means, common to the art, to remove radionuclidic impurities prior to quality control testing or administering the compound to a patient. One useful device for purification, which may be present in a kit, is a filter column. One useful filter material for purification is Dowex 1 ion exchange resin.

After the radiolabeled has been mixed and preferably purified, it may be directly administered in vivo to a patient. Preferably, the compound is first quality control tested in accordance with the invention to assure that the radiolabeled compound will react with a patient's tumor, and to assure that the selection of the monoclonal antibody and the compounding of the radiolabeled compound were properly and adequately performed.

The quality control testing kit of the present invention comprises at least one test area (the tumor test area), and preferably a negative control test area and a positive control test area.

The tumor test area contains a binding material which will bind a sample of tumor homogenate. One such binding material, useful for binding the tumor sample to the test area, is nitrocellulose filter paper. The tumor sample is prepared, and bound or fixed to the tumor test area of the quality control apparatus in a manner similar to that used in the selection method and apparatus. The test area is then coated or blocked with excessive antigenic material, such as bovine serum albumin.

The tumor test area on the quality control apparatus may be prepared at the same time as the tumor test area on the selection apparatus. A tumor sample could be bound to the quality control test area, and then stored for at least several months in cold temperatures prior to useage. This would eliminate the need to subject a patient to two biopsy procedures; one at the time a monoclonal antibody is selected, and again when the radiolabeled compound is quality control tested. On the other hand, it may be desirable to obtain a subsequent tumor specimen from a patient if there has been a great deal of time between the selection stage and the quality control testing stage to assure that the tumor has not changed its character and is still reactive with the selected antibody or antibodies.

In the quality control testing method of the invention, a small sample of the radiolabeled compound is placed on a tumor test area. One means of placing the compound sample on the test area is to use a small syringe or eye-dropper. The sample is fixed to the test area. Fixing is preferably achieved by incubation, such as by incubating in a humid environment at about 25° C. for about 30 minutes. The radioactivity present on the test area, due to the radiolabeled compound, is then measured by means of a radiation detector. Radiation may be measured by means, common to the art, such as with a gamma counter or an ionization chamber. The tumor test area is then washed to remove any compound which has not reacted with the tumor sample. After washing, the radioactivity present on the washed tumor test area is again measured by means of a radiation detector. The percent immunoreactivity of the compound with the tumor sample is calculated by dividing the measure of radioactivity present after washing by the measure of radioactivity before washing. This percentage should be very high for highly reactive compounds, and moderately high for moderately reactive compounds. If the percentage is low, the radiolabeled compound should not be administered to a patient. Reasons for obtaining a low percentage may include the following: (1) the monoclonal antibody was not properly selected; (2) the radiolabeled compound was not properly prepared; (3) the tumor sample was not adequate (stored too long or not bound properly); or (4) a new tumor biopsy sample is no longer reactive with a previously selected monoclonal antibody.

Preferably, the quality control testing kit further comprises a negative control test apparatus and/or a positive control test apparatus. A negative control apparatus contains a test area with an antigenic substance, such as bovine serum albumin, which will not react or will insubstantially react with the radiolabeled compound. The radiolabeled compound will contain at least one of the monoclonal antibodies present in the selection apparatus of the kit, and thus the antigenic substance chosen should not react with any of the panel of monoclonal antibodies which might be compounded, or which are present in the selection apparatus of the kit. The positive control test apparatus contains a test area which binds an antigenic substance, such as a tumor homogenate xenograft, which should react with the radiolabeled compound if the compound has been properly prepared. If there is more than one monoclonal antibody present in the radiolabeled compound, a separate positive control test area should be provided to correspond to each monoclonal antibody.

In the preferred quality control testing method of the invention, a small sample of the radiolabeled compound is placed on the negative and positive control test areas at approximately the same time as the compound sample is placed on the tumor test area. The negative and positive control areas are treated in the same manner as the tumor test area; the radioactivity present on the test areas are measured, the test areas are washed to remove unreacted compound, and the radioactivity present is again measured after washing. For the positive control area, the radioactivity percentage should be high. If the percentage is not high, the radiolabeled compound should not be administered to the patient. A low percentage on the positive control test area might be an indication of damaged antibodies, non-bonding of the radionuclide material to the antibody, or an error in the selection, compounding or quality control testing. For the negative control test area, the radioactivity percentage should be low to zero. A high percentage on the negative control test area indicates that an error in compounding or in quality control testing has been made. The material should be recompounded and/or retested before it is administered to the patient.

An example of hypothetical reactivity percentages which could be obtained in a quality control test of the invention for a radiolabeled compound containing one monoclonal antibody, for illustrative purposes only, is as follows: (1) The immunoreactivity percentage of the tumor test area should range between 70% to 100%; 2) the percentage reactivity of the negative control area should range between 0% to 15%; and 3) the reactivity percentage of the positive control area should range between 85% to 100%. An example of hypothetical reactivity percentages which could be obtained in a quality control test of the invention for a radiolabeled compound containing two monoclonal antibodies (50% of antibody A and 50% of antibody B), for illustrative purposes only, is as follows: 1) The immunoreactivity percentage of the tumor test area should range between 70% to 100%; 2) the reactivity percentage of the negative control test area should range between 0% to 15%; 3) the reactivity percentage of the positive control test area for antibody A should range between 35% to 50%; and 4) the reactivity percentage of the positive control area for antibody B should range between 35% to 50%.

In kit form, the quality control test apparatus may be separate strips which could be torn or separated for ease in radiation detection. The quality control apparatuses may be useful separately or as a kit, and in conjunction with the selection and compounding apparatuses of the invention to form a complete kit.

The preferred kit of the invention for the selection, compounding, and quality control testing of a radiolabeled drug or compound for in vivo use in a patient to detect or treat cancer comprises the following:

(a) A selection apparatus, comprising; an insert with at least two projections, each projection containing a tumor test area; and a matching receptacle for receiving the insert and which contains at least two antibodies or antibody fragments which are potentially reactive with the tumor specimen;

(b) A compounding apparatus comprising; a receptacle for receiving and mixing the selected antibody or antibodies, a labeling reagent and a radionuclide to form a radionuclidic compound; and a filter column for purifying the formed radionuclidic compound; and (c) Quality control apparatuses for conducting at least three tests, one apparatus comprising at least one negative control test area which contains an antigenic material which is unreactive with any of the panel of the antibodies contained in the selection apparatus; one apparatus comprising at least one tumor test area which should react substantially with the radiolabeled compound if the antibodies have been properly selected and if the radiolabeled compound has been properly prepared, and one apparatus comprising at least one positive control test area for each of the panel of antibodies contained in the selection apparatus which should react with the radiolabeled compound to the extent that the corresponding antibody is present in the compound.

The kit and methods of the invention can be used to compound a radiolabeled drug or compound for cancer detection or for immunotherapy. In cancer detection, the drug is administered to a patient and the patient is imaged with an imaging device, such as a gamma-ray imaging device or a contrast enhanced nuclear magnetic resonance imaging device, to determine the extent and location of cancerous tumors. In immunotherapy, the drug or compound is administered to a patient for treatment of the cancerous tumor or tumors.

EXAMPLE 1

This example describes a method and apparatus for the testing of a panel of monoclonal antibodies potentially reactive with human colon tumors in order to select those antibodies which are appropriate for compounding a tumor-imaging or therapeutic radiopharmaceutical which will be specific for a given individual patient. The apparatus comprises an insert and a receptacle.

The insert has seven teethlike projections, each projection containing three test areas for indicating antigen-antibody reactions. The three test areas on each projection are: (1) a negative control area; (2) an antigen-antibody test area for the tumor specimen; and (3) a positive control area. Carcinoembryonic antigen (CEA) is bound to the positive control areas of the first four projections. Colon-ovarian tumor antigen (COTA) is bound to the positive control area of the fifth projection; colon specific antigen protein (CSAp) is bound to the positive control area of the sixth projection; and human chorionic gonadotrophin is bound to the positive control area of the seventh projection.

The receptacle is a container with four rows of seven compartments in each row. The first row of seven compartments contains 0.5 milliliters each of 1% by weight bovine serum albumin; the second row of seven compartments contains 0.5 milliliter solutions of each of a 0.001% by weight solution of seven different monoclonal antibodies in the following order: Anti-CEA, determinant 1; Anti-CEA, determinant 2; Anti-CEA, determinant 3; Anti-CEA, determinant 4; anti-COTA; anti-CSAp; and anti-hCG-beta. The third row of seven compartments contains a 0.1% by weight solution of goat antimouse IgG - horseradish peroxidase conjugate. The fourth row of seven compartments contains a 0.1% by weight solution of hydrogen peroxide in water.

A colon tumor specimen obtained at surgery is homogenized in a phosphate buffered saline, having a pH of 7.4 and diluted to make a 1:9 dilution of the specimen. 0.05 milliliter aliquots of the homogenized solution are placed on the test area of each of the seven projections of the insert reserved for tumor specimen samples. The insert is allowed to stand for 30 minutes in a humid chamber at 25° C. The insert is then placed in the first row of compartments of the receptacle, containing the bovine serum albumin solution, and allowed to incubate in the receptacle for 30 minutes at 25° C. The insert is removed and washed to remove any unfixed antigenic materials. The insert is then placed into the second row of compartments of the receptacle and allowed to incubate for 30 minutes at 25° C. to permit the reaction of the various different monoclonal antibodies. The insert is then washed and placed into the third row of compartments of the receptacle, containing the goat antimouse IgG - horseradish peroxide conjugate, and allowed to incubate for 30 minutes at 25° C. The insert is then washed and placed into the fourth row of compartments in the receptacle, containing the hydrogen peroxide solution, and allowed to incubate for 10 minutes at 25° C. to allow the areas to which antibody has become bound to develop a darkened appearance. The insert is removed and washed to remove any residual hydrogen peroxide solution and allowed to dry. The antibodies which have reacted with the tumor are indicated by the darkened areas on the projections of the insert. The negative control area shows slight or no darkening when the method and apparatus has been used correctly. Excessive darkening of the negative control area indicates a problem with the assay. The positive control area indicates an antigen-antibody reaction by darkening. Zero or slight darkening of the positive control area indicates a problem with the assay.

EXAMPLE 2

This example describes an apparatus and method for the testing of a panel of monoclonal antibodies potentially reactive with human breast tumors in order to select those antibodies which are appropriate for compounding a tumor-imaging or therapeutic radiopharmaceutical which is specific for a given individual patient. The insert is made to have ten teethlike projections, each projection containing three test areas for indicating antigen-antibody reactions. The three test areas on each projection are: (1) a positive control area; (2) an antigenantibody test area for the tumor specimen; and (3) a negative control area. The following antigens are bound on the positive control areas: Human mammary epithelial antigen (HME-Ag) (46,000 daltons) is bound to the first projection; HME-Ag (70,000 daltons) is bound to the second projection; HME-Ag (150,000 daltons) is bound to the third projection; CEA is bound to the fourth, fifth, sixth, and seventh projections; antigen recognized by monoclonal antibody B6.2 is bound to the eighth projection; antigen recognized by monoclonal antibody B72.3 is bound to the ninth projection; and human chorionic gonadotrophin is bound to the tenth projection. (The following references provide information on the specific antigens used for each projection: (1) HME-Ags: See "Circulating Human Mammary Epithelial Antigen in Breast Cancer," by R.L. Ceriani, M. Sasaki, H. Susman, W.M. Wara, and E.W. Blank, *Proc. Natl. Acad. Sci*, Vol. 79, pp. 5420-5424, (1982); (2) Antigens reactive with B6.2 and B72.3: See "Definition of Antigenic Heterogeneity and Modulation around Human Mammary Carcinoma Cell Populations Using Monoclonal Antibodies to Tumor-Associated Antigens," by P. Horan Hand, M. Nuti., D. Colcher and J. Schlom, *Cancer Res.* Vol. 43, pp. 728-735, (1983).)

The receptacle is a container with four rows of ten compartments in each row. The first row of 10 compartments contains 0.5 milliliters each of a 1% by weight bovine serum albumin; the second row of 10 compartments contains 0.5 milliliters each of a 0.001% by weight solution of ten different monoclonal antibodies in the following order: (1) Anti-HME-Ag-46,000; (2) Anti-HME-Ag-70,000; (3) Anti-HME-Ag-150,000; (4) Anti-CEA, determinant 1; (5) Anti-CEA, determinant 2; (6) Anti-CEA,determinant 3; (7) Anti-CEA, determinant 4; (8) B6.2; (9) B72.3; and (10) anti-hCH-beta. The third row of ten compartments contains a 0.1% by weight solution of goat antimouse IgG-horseradish peroxidase conjugate. The fourth row of ten compartments contains a 0.1% by weight solution of hydrogen peroxide in water.

A breast tumor specimen obtained at surgery or needle biopsy is homogenized in a phosphate buffered saline solution, having a pH of 7.4 and diluted to make a 1:9 dilution of the specimen. 0.05 milliliter aliquots of the homogenized solution are placed on the test area of each of the ten projections of the insert reserved for tumor specimen samples. The insert is allowed to stand for 30 minutes in a humid chamber at 25° C. The insert is then placed in the first row of compartments of the receptacle, containing the bovine serum albumin solution, and allowed to incubate in the receptacle for 30 minutes at 25° C. The insert is removed and washed to remove any unfixed antigenic materials. The insert is then placed into the second row of compartments of the receptacle, and allowed to incubate for 30 minutes at 25° C. to permit the reaction of the various different monoclonal antibodies with the tumor specimens. The insert is removed from the receptacle and washed to remove any unreacted antibodies. The insert is then placed into the third row of compartments of the receptacle, containing the goat antimouse IgG - horseradish peroxidase conjugate, and allowed to incubate for 30 minutes at 25° C. The insert is removed and washed to remove any residual second antibody-horseradish peroxidase. The insert is then placed into the fourth row of compartments in the receptacle, containing a hydrogen peroxide solution, and allowed to incubate for 10 minutes to allow the areas to which antibody has become bound to develop a darkened appearance. The insert is removed and washed to remove any residual hydrogen peroxide solution and allowed to dry. The antibodies which have reacted with the tumor are indicated by the darkened areas on the projections of the insert. The negative control area shows slight or no darkening when the method and apparatus has been used correctly. Excessive darkening of the negative control area indicates a problem with the assay. The positive control area indicates an antigen-antibody reaction by darkening. Zero or slight darkening of the positive control area indicates a problem with the assay.

EXAMPLE 3

This example describes an apparatus and method for the quality control testing of a radiolabeled compound. A flat, plastic strip which has a circular cutout at one end is used as a test strip. The cutout is backed with an absorbant material known to bind proteins such as nitrocellulose paper. This cutout is loaded with 5 microliters of a sample of tumor homogenate. To prepare the tumor homogenate, a fresh sample of tumor obtained from surgical or needle biopsy is mixed with 9 parts of phosphatebuffered, 0.9% saline solution and homogenized. After adding the tumor homogenate, the spot is allowed to dry and the strip is allowed to soak in a solution of bovine serum albumin to block additional binding sites on the absorbant material.

Additional test strips have been preloaded with a known antigen (for use as a positive control) or with bovine serum albumin (for use as a negative control) are also used in an assay for immunoreactivity.

The prepared antibody dosage form in the radiolabeled compound is tested by spotting 1-10 microliters of the radiolabeled drug (or a dilution of the drug made in 0.1% bovine serum albumin in 0.9% saline solution) onto the cutout of the strip containing tumor homogenate. Similar aliquots of the drug are spotted onto the cutouts of both the positive and the negative control test areas. If the drug has been compounded using more than one monoclonal antibody, then an additional positive control is used for each additional antibody. The positive control test areas are matched (or known to react with) a given monoclonal antibody. After the tests areas are spotted with the aliquots of the tumor homogenate, they are allowed to react for 1 to 60 minutes in a humid environment. Next, they are assayed in a radiation detector. After the assay, they are washed to remove unreacted antibody and assayed again. The amount of radioactivity which is retained on the strip containing the sample of tumor homogenate is taken as a measure of the immunoreactivity of the dosage form. The positive and the negative control strips are used to verify that the assay has been carried out correctly; they are used to quality control the assay. The negative control test area should indicate zero or minimal reactivity with the drug whereas the positive control test area should indicate a substantial reactivity with the drug.

For antibody dosage forms that do not contain radioactivity, a two step assay is required. After the strips have been spotted with aliquots of the drug and allowed to react for 1 to 60 minutes in a humid environment, they are washed to remove unreacted antibody. A radiolabeled second antibody which reacts with the antibodies used for drug compounding, such as I-125 labeled goat anti-mouse antibodies are added to the previous spots and the strips allowed to incubate again for 1 to 60 minutes. During this time they are assayed for radioactivity. After the incubation and the assay, they are washed to remove unreacted second antibody and assayed again. The percentage binding of the radioactivity is measured for each strip. The quality control determination is made based on the relative binding of the radioactivity to the tumor sample compared to the positive control. This result is compared to previously measured values. This assay measures relative immunoreactivity rather than absolute immunoreactivity as was the case previously cited, i.e., the direct assay.

Accordingly, a method and kit for the compounding of selected monoclonal antibodies useful in the diagnosis and treatment of individual tumors has been discovered. Use of the selection method and apparatus indicate which antibodies show an antigenantibody reaction and thus should be used for compounds or drugs to be administered to the patient. Use of the compounding method and apparatus enable the compounding of the selected monoclonal antibody or antibodies with a labeling reagent and a radionuclide. Use of the quality control testing apparatus and method of the invention assure that the radiolabeled compound has been properly prepared and will react in vivo with a patient's tumor. Compounds which are reactive with a given patient's tumor can thus be determined prior to administering the compound to the patient, using the kit and methods of the invention.

I claim:

1. A method to select, formulate and compound a variable formula patient specific monoclonal antibody-based drug for use in in vivo cancer detection or therapy for a specific patient, comprising the following steps:
   (a) preselecting a panel of a plurality of monoclonal antibody components, the monoclonal antibody components comprising members selected from the group consisting of whole monoclonal antibodies and monoclonal antibody fragments, the monoclonal antibody components being predetermined to be specific to tumor associated antigens of a cancer type to be detected or treated;
   (b) obtaining at least one first solid tumor specimen, from the specific patient, of the cancer type to be detected or treated;
   (c) dividing the first solid tumor specimen into a number of aliquots corresponding to the number of monoclonal antibody components in the preselected panel;
   (d) subjecting each monoclonal antibody component in the preselected panel to a different aliquot of the specific patient's first solid tumor specimen and allowing the preselected panel of monoclonal antibody components to bind to tumor associated antigens present in the specific patient's first solid tumor specimen;
   (e) determining which, if any, of the monoclonal antibody components in the preselected panel bind to tumor associated antigens present in the specific patient's first solid tumor specimen; and
   (f) choosing more than one monoclonal antibody component, if the chosen monoclonal antibody components are determined in step (e) to bind to tumor associated antigens present in the specific patient's first solid tumor specimen, for use in formulating and compounding a variable formula monoclonal antibody-based drug for use in in vito cancer detection or therapy for the specific patient.

2. A method in accordance with claim 1 wherein prior to step (c), the specific patient's first solid tumor specimen is homogenized.

3. A method in accordance with claim 1 wherein the preselected monoclonal antibody components in the panel are lyophilized.

4. A method in accordance with claim 3 wherein the lyophilized monoclonal antibody components are reconstituted into solution using serum from the specific patient.

5. A method in accordance with claim 1 further comprising the following additional steps:
   (g) providing a preselected negative control antigenic substance, being predetermined to be non-specific to all of the preselected monoclonal antibody components;
   (h) allowing the preselected negative control antigenic substance to be exposed to and bind to the preselected monoclonal antibody components; and
   (i) determining whether the preselected negative control antigenic substance binds to any or all of the preselected monoclonal antibody components;
   whereby if the preselected negative control antigenic substance fails to bind to any of the preselected monoclonal antibody components, the method has been performed correctly.

6. A method in accordance with claim 1 further comprising the following additional steps:
   (g) for each preselected monoclonal antibody component, providing a preselected positive control antigenic substance being predetermined to be specific to the corresponding preselected monoclonal antibody component;
   (h) allowing the preselected positive control antigenic substances to be exposed to and bind to the corresponding preselected monoclonal antibody components; and
   (i) determining whether the preselected positive control antigenic substances bind to the corresponding preselected monoclonal antibody components;
   whereby if the preselected positive control antigenic substances bind to the preselected corresponding monoclonal antibody components, the method has been performed correctly.

7. A method in accordance with claim 6 further comprising the following additional steps:
   (j) providing a preselected negative control antigenic substance, being predetermined to be non-specific to all of the preselected monoclonal antibody components;
   (k) allowing the preselected negative control antigenic substance to be exposed to and bind to the preselected monoclonal antibody components; and
   (l) determining whether the preselected negative control antigenic substance binds to any or all of the preselected monoclonal antibody components;
   whereby if the preselected negative control antigenic substance fails to bind to any of the preselected monoclonal antibody components, the method has been performed correctly.

8. A method in accordance with claim 1 further comprising the additional step of compounding the chosen monoclonal antibody components in step (f) to form a monoclonal antibody-based drug product.

9. A method in accordance with claim 8 wherein the chosen monoclonal antibody components are conjugated with at least one chemical agent.

10. A method in accordance with claim 9 wherein the chemical agent comprises a member selected from the group consisting of radionuclides, chemotherapy agents, and toxins.

11. A method in accordance with claim 8 wherein, subsequent to the compounding step, the monoclonal antibody-based drug product is subjected to a patient-specific quantitative immunoreactivity test to determine a quantitative reactivity of the monoclonal antibody-based drug product to tumor associated antigens of the tumor of the specific patient.

12. A method in accordance with claim 11 wherein the compounded monoclonal antibody-based drug product is radiolabeled with a radionuclide and the patient-specific quantitative immunoreactivity test comprises the following steps:
   (a) providing a second solid tumor specimen from the specific patient, the second solid tumor specimen having a multiplicity of binding sites for binding with corresponding antibody binding sites;
   (b) introducing a quantity of radiolabeled monoclonal antibody-based drug product to the second solid tumor specimen to form a first combination;
   (c) allowing the quantity of radiolabeled monoclonal antibody-based drug product to bind to the second solid tumor specimen in the first combination;
   (d) measuring a radioactivity of the quantity of radiolabeled monoclonal antibody-based drug product at any step prior to step (d);
   (e) removing from the first combination substantially all radionuclides except those in the radiolabeled monoclonal antibody-based drug product bound to the second solid tumor specimen in the first combination;
   (f) measuring a radioactivity of the resulting first combination of the radiolabeled monoclonal antibody-based drug product and second solid tumor specimen after removal of substantially all radionuclides except those in the radiolabeled monoclonal antibody-based drug product bound to the second solid tumor specimen; and
   (g) determining quantitatively the reactivity of the radiolabeled monoclonal antibody-based drug product to tumor associated antigens of the tumor of the specific patient by comparing the radioactivity measured in step (d) with the radioactivity measured in step (f).

13. A method in accordance with claim 13 wherein the patient-specific quantitative immunoreactivity test comprises the following additional steps:
   (h) providing a portion of a preselected positive control antigenic substance being determined to be specific to the monoclonal antibody component in the radiolabeled monoclonal antibody-based drug product, the portion having a multiplicity of binding sites for binding with corresponding antibody binding sites;
   (i) introducing a quantity of radiolabeled monoclonal antibody-based drug product to the portion of the preselected positive control antigenic substance to form a second combination;
   (j) allowing the quantity of radiolabeled monoclonal antibody-based drug product to bind to the portion of the preselected positive control antigenic substance in the second combination;
   (k) measuring a radioactivity of the quantity of radiolabeled monoclonal antibody-based drug product at any step prior to step (k);
   (l) removing from the second combination substantially all radionuclides except those in the radiolabeled monoclonal antibody-based drug product bound to the preselected positive control antigenic substance in the second combination;
   (m) measuring a radioactivity of the resulting second combination of the radiolabeled monoclonal antibody-based drug product and preselected positive control antigenic substance after removal of substantially all radionuclides except those in the radiolabeled monoclonal antibody-based drug product bound to the preselected positive control antigenic substance; and
   (n) validating that the method was conducted properly and determining quantitatively the reactivity of the radiolabeled monoclonal antibody-based drug product by comparing the radioactivity measured in step (k) with the radioactivity measured in step (m).

14. A method in accordance with claim 13 wherein the patient-specific quantitative immunoreactivity test comprises the following additional steps:
   (o) providing a portion of a preselected negative control antigenic substance being determined to be non-specific to the monoclonal antibody component in the radiolabeled monoclonal antibody-based drug product;
   (p) introducing a quantity of the radiolabeled monoclonal antibody-based drug product to the portion of the preselected negative control antigenic substance to form a third combination;
   (q) allowing the quantity of radiolabeled monoclonal antibody-based drug product to bind to the portion of the preselected negative control antigenic substance in the third combination;
   (r) measuring a radioactivity of the quantity of the radiolabeled monoclonal antibody-based drug product at any step prior to step (r);
   (s) removing from the third combination substantially all radionuclides except those in the radiolabeled monoclonal antibody-based drug product bound to the preselected negative control antigenic substance;
   (t) measuring a radioactivity of the resulting third combination of the radiolabeled monoclonal antibody-based drug product and preselected negative control antigenic substance after removal of substantially all radionuclides except those in the radiolabeled monoclonal antibody-based drug product bound to the preselected negative control antigenic substance; and
   (u) validating that the method was conducted properly and determining quantitatively the non-specific reactivity of the radiolabeled monoclonal antibody-based drug product by comparing the radioactivity measured in step (r) with the radioactivity measured in step (t).

* * * * *